United States Patent [19]

Kissinger

[11] Patent Number: 4,876,395
[45] Date of Patent: Oct. 24, 1989

[54] PROCESS FOR COLOR STABILIZATION OF BISPHENOL-A

[75] Inventor: Gaylord M. Kissinger, Evansville, Ind.

[73] Assignee: General Electric Company, Mt. Vernon, Ind.

[21] Appl. No.: 217,722

[22] Filed: Jul. 11, 1988

[51] Int. Cl.$^4$ .............................................. C07C 39/12
[52] U.S. Cl. .................................... 568/728; 568/724; 568/727
[58] Field of Search ................ 568/702, 724, 728, 727

[56] References Cited

U.S. PATENT DOCUMENTS 2,716,139  8/1955  Dietzler ................................. 568/702
4,443,635  4/1984  McLaughlin ......................... 568/728
4,766,254  8/1988  Faler et al. ........................... 568/702

Primary Examiner—Werren B. Lone

Attorney, Agent, or Firm—Martin B. Barancik

[57] ABSTRACT

A process which comprises
(a) contacting an excess of a phenol with a ketone in the presence of an acidic ion exchange resin catalyst;
(b) recovering thereafter a stream from an acidic ion exchange resin catalyst, said stream including the dihydric phenol, unreacted phenol, isomers of the desired dihydric phenol and acid impurities derived from the acidic ion exchange resin catalyst;
(c) removing a major portion of the desired dihydric phenol from the stream of (b);
(d) adding to the dihydric phenol effective quantities of a Group II-a metal or transition metal of oxidation number +2 carbonate to color stablize the dihydric phenol;
(e) recovering the solid dihydric phenol and the metal carbonate.

11 Claims, No Drawings

PROCESS FOR COLOR STABILIZATION OF BISPHENOL-A

BACKGROUND OF THE INVENTION

The dihydric phenols have achieved significant success in their commercial applications. Dihydric phenols are useful in the commercial manufacture of various polymers including the polyarylates, polyamides, epoxies, polyetherimides, polysulfones and the polycarbonates. Significant attention has been directed to the commercial preparations of the dihydric phenols. For many years it has been well known that the acid catalyzed reaction of phenol with specific aldehyde or ketone could prepare the 4,4'-dihydric phenol with specific groups derived from the aldehyde or the ketone connecting the two phenolic rings. In particular when phenol is reacted with acetone, the dihydric phenol 4,4'(dihydroxyphenyl)propane-2, hereafter known as bisphenol-A is formed. This has particular utility in polycarbonates, polyarylates and copolyestercarbonates as well as epoxies. In order to make certain polymers, in particular the polycarbonates, the bisphenol-A must be particularly pure, for example, as measured by color. Additionally, the process should be particularly efficient since the dihydric phenol costs contribute substantially to the cost of the final polymer. Therefore much attention has been directed to the recovery of bisphenol-A after preparation.

Various catalytic systems for acid catalysis of the reaction between phenol and bisphenol-A have been investigated and used commercially. At one time the hydrochloric acid catalyzed process was used in a significant number of commercial facilities. However the corrosion caused by the hydrochloric acid on reactors and pre and post reaction equipment left much to be desired as far as replacement economics was concerned. Recently, substantial attention has been placed on using an ion exchange resin catalyst system since it does not have a significant acid corrosion problem. However it has recently been discovered in our equipment that the usual processing techniques for recovery of bisphenol-A from recovery streams after preparation with the ion exchange catalyst cannot be practiced in the same manner as when using the hydrochloric acid catalyst system. The quality of the bisphenol-A which could be recovered was sufficiently lessened as measured by color. Color is a very important property of the final polymers which are prepared from the bisphenol-A as well as the bisphenol-A itself. For example, bisphenol-A polycarbonate is known to be clear and colorless. Additionally, the yield of the bis-phenol-A was reduced significantly due to increased presence of isomers.

It has now been discovered that a dihydric phenol can be successfully recovered in substantial quantities from an ion exchange catalyzed reaction of a phenol with a ketone, phenol per se with acetone, by utilizing a relatively simple treatment with a specific basic system. Degradation of the dihydric phenol to isomeric forms is inhibited and the color of the dihydric phenol stabilized and generally improved.

SUMMARY OF THE INVENTION

In accordance with the invention, there is a process which comprises (a) contacting an excess of a phenol with a ketone in the presence of an acidic ion exchange resin catalyst;

(b) recovering thereafter a stream from an acidic ion exchange resin catalyst, said stream including the dihydric phenol, unreacted phenol, isomers of the desired dihydric phenol and acid impurities derived from the acidic ion exchange resin catalyst;

(c) removing a major portion of the desired dihydric phenol from the stream of (b);

(d) adding to the dihydric phenol effective quantities of a Group II-a metal or transition metal of oxidation number +2 carbonate to color stabilize the dihydric phenol;

(e) recovering the solid dihydric phenol and the metal carbonate.

In further accordance with the invention there is a process for preparing and isolating a dihydric phenol from the reaction of a phenol and a ketone in the presence of an acidic ion exchange resin catalyst, the improvement comprising the addition of sufficient quantities of a Group II-a metal or transition metal of oxidation number +2 carbonate to a major quantity of the dihydric phenol and thereafter recovering the dihydric phenol and metal carbonate.

Another aspect of the invention is composition comprising a solid dihydric phenol, preferably bis-phenol-A in admixture with a Group II-a metal or transition metal of oxidation number +2 carbonate.

DETAILED DESCRIPTION OF THE INVENTION

The most well known dihydric phenol is bisphenol-A. The invention shall be further described in detail with the production of bisphenol-A. However, any other dihydric phenol is anticipated to have also these problems if made from the reaction of a phenol with an acetone and an acidic ion exchange resin catalyst system which has produced acidic impurities. Examples of such dihydric phenol include phenols disclosed in U.S. Pat. Nos. 2,999,835; 3,028,365; 3,334,154 and 4,131,575.

Phenol and acetone are passed into a reactor having an acidic ion exchange resin catalyst system. Such catalyst system can be an Amberlite type resin obtained from Rohm and Haas. This resin has a styrenic backbone with pendant $SO_3H$ groups which provide the acidic character to the resin. Usually the styrene is crosslinked with a small quantity of divinyl benzene or other crosslinking chemical. This addition of a crosslinker appears to provide structural strength and rigidity to the catalyst. The phenol in excess, together with the acetone, is passed over the acidic ion exchange resin. Other ion exchange resins can also be used although it is preferable to use the styrenic backbone crosslinked with the difunctional monomer and having $SO_3H$ groups pendant from the aromatic nucleus of the styrene moiety.

The stream coming off the catalyst has the bisphenol-A, excess phenol, isomers of bisphenol-A, isopropenyl phenol (IPP), chromans (which are addition products of various bisphenols), spiro biindanes and other side reaction products of the reaction of the phenol with the acetone. Additionally present in the stream coming off the ion exchange resin was the unrealized formation of acidic impurities derived from the acidic ion exchange resin. Although not to be held by this theory of the invention, it is believed that acidic ion exchange resins may not be fully polymerized and that held within the network of the solid resin are acidic impurities of an oligomeric nature. When such resins are contacted with appropriate reactants and products, such oligomeric acidic impurities can be leached therefrom and join the product stream. At various points within the downstream processing such acidic impurities may build up to such an extent that they catalyze undesired reactions between the materials present in the stream.

At this point a substantial amount of the bis-phenol-A is removed from the stream. Bisphenol-A is unlike other dihydric phenols in that it forms a stable addition adduct with phenol. This physical addition adduct is utilized in the removal of the bisphenol-A from the stream. Various recovery processes are then utilized to separate the bisphenol-A from the phenol, such as nitrogen desorption at the vapor temperature of phenol, finally producing a high quality solid bis-phenol-A. Rather than using the adduct, a distillation train can be employed to separate the dihydric phenol from the other components of the stream.

It has been observed that bisphenol-A prepared in this manner has higher degradation products associated with it such as isopropenyl phenol, a highly colored material, and various linear and cyclic dimers. Additionally initial and final absorbance values of the bisphenol-A are significantly higher than expected. BPA product assay (% BPA) was also lower than expected. These unexpected problems in the product BPA were substantially reduced by adding acid neutralizing effective amounts of a carbonate of a Group II a metal or transition metal of oxidation number +2. Examples of such metals include magnesium, calcium, barium, manganese, cobalt, nickel, copper, zinc and the like. Barium carbonate is preferred.

The metal carbonate is added to the bisphenol-A when it has been substantially separated from the stream coming off the catalyst. For example, if using a phenol-bisphenol-A adduct separation procedure it can be added when the adduct is formed or when the adduct is melted, or even when the phenol is being separated from the adduct. Since it is undesirable for unreacted metal carbonate or metallic products of neutralization to be in contact with the reactor resin, the metal carbonate is added the bisphenol-A at a time when it will not enter into recycle stream which would pass over the catalyst.

The quantity of metallic carbonate which may be present should be sufficient to stabilize the bis-phenol-A as to color and % BPA in final product essay. This depends upon the quantity of acidic impurities which may be present in the stream and the efficiency of the contact of the metallic carbonate with the acidic impurities. We have found that from about 0.002 to about 0.2 weight percent of barium carbonate calculated on the basis of the total stream weight is sufficient.

Below are examples of the invention. These examples are intended to be illustrative of the scope of the invention and not to limit it therein.

In the examples below, BPA is bisphenol-A and IPP is isopropenyl phenol.

EXAMPLE 1

Bisphenol-A is prepared by an ion exchange resin system and goes through an adduct isolation procedure. Measurement of color quality of the bisphenol-A by ultraviolet light absorbance at 350 nm after heating the recovered solid bisphenol-A at 140° C. for five hours in an air circulating oven (final absorbance) showed a value in absorbance units of 0.42. This indicates thermal instability. The usual values for BPA in this test system is about 0.15 to 0.20. At this time the IPP level, a serious color contaminant was 0.09%. The usual values for IPP is about 0.005 to 0.006% of the product. Barium carbonate is added to the adduct melter at a 0.01 weight percent of the adduct melt. The final absorbance of the bisphenol-A is now significantly reduced to 0.135. The weight percent of IPP was significantly reduced to 0.005.

What is claimed is:

1. A process which comprises
   (a) contacting an excess of phenol with acetone in the presence of an acidic ion exchange resin catalyst;
   (b) recovering thereafter a stream from an acidic ion exchange resin catalyst, said stream including bisphenol-A unreacted phenol, isomers of bisphenol-A and acid impurities derived from the acidic ion exchange resin catalyst;
   (c) removing a major portion of the bisphenol-A from the stream of (b);
   (d) adding to the bisphenol-A effective quantities of a Group II-a metal or transition metal of oxidation number +2 carbonate to color stabilize the bisphenol-A;
   (e) recovering the solid bisphenol-A and the metal carbonate.

2. The process in acordance with claim 1 wherein the cation is selected from the group consisting of magnesium, calcium, barium, manganese, cobalt, nickel, copper and zinc.

3. The process in accordance with claim 2 wherein the cation is zinc, manganese, magnesium, calcium and barium.

4. The process in accordance with claim 3 wherein the cation is barium.

5. A process for preparing and isolating bisphenol-A from the reaction of phenol and acetone in the presence of an acidic ion exchange resin catalyst, the improvement comprising the addition of sufficient quantities of a Group II-a metal or transition metal of oxidation number +2 carbonate to color stabilize a major quantity of the bisphenol-A and thereafter recovering the bispheol-A and metal carbonate.

6. The process in accordance with claim 5 wherein the metal is selected from the group consisting of magnesium, calcium, barium, manganese, cobalt, nickel, copper and zinc.

7. The process in accordance with claim 6 wherein the metal is zinc, manganese, magnesium, calcium or barium.

8. The process in accordance with claim 7 wherein the metal is barium.

9. A composition comprising solid bisphenol-A in admixture with a color stabilizing quantity of Group II-a metal or transition metal of oxidation number +2 carbonate.

10. The composition in accordance with claim 9 wherein the metal is selected from the group consisting of magnesium, calcium, barium, manganese, cobalt, nickel, copper and zinc.

11. The composition in accordance with claim 10 wherein the metal is barium.

* * * * *